United States Patent

Blankenburg et al.

[11] Patent Number: 6,103,820
[45] Date of Patent: *Aug. 15, 2000

[54] PREPARATION OF WATER-SOLUBLE COPOLYMERS OF AT LEAST ONE WATER-SOLUBLE N-VINYLLACTAM AND AT LEAST ONE HYDROPHOBIC COMONOMER

[75] Inventors: Rainer Blankenburg, Ludwigshafen; Stephan Kothrade, Limburgerhof; Axel Sanner, Frankenthal, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/805,547

[22] Filed: Feb. 25, 1997

[30] Foreign Application Priority Data

Mar. 13, 1996 [DE] Germany ............... 196 09 864

[51] Int. Cl.[7] ........................................ C08K 3/20
[52] U.S. Cl. .................... 524/767; 524/808; 526/264
[58] Field of Search ............... 526/264; 524/767, 524/808

[56] References Cited

U.S. PATENT DOCUMENTS

| | | | |
|---|---|---|---|
| 2,982,762 | 5/1961 | Voeks et al. | 526/264 |
| 3,862,915 | 1/1975 | Fried et al. | 260/29 |
| 4,520,179 | 5/1985 | Barabas et al. | 526/212 |
| 4,554,311 | 11/1985 | Barabas et al. | 524/808 |
| 4,786,699 | 11/1988 | Nuber et al. | 526/229 |
| 5,502,136 | 3/1996 | Zhong et al. | 526/264 |
| 5,506,315 | 4/1996 | Meyer et al. | 526/89 |

OTHER PUBLICATIONS

Fikentscher, *Cell. Chemie*, 13, 1932, pp. 58–64, 71 and 74.
*Kirk–Othmer Enc. of Chem. Tech.*, 2nd Ed., vol. 21, 1970, pp. 427–440.

*Primary Examiner*—Bernard Lipman
*Attorney, Agent, or Firm*—Keil & Weinkauf

[57] ABSTRACT

The present invention relates to a novel process for preparing water-soluble copolymers of at least one water-soluble N-vinyllactam of the formula I

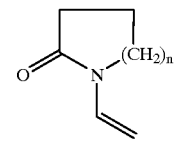

where n=1 or 2, and at least one hydrophobic comonomer having a water-solubility of 1 to 85 g/l, by free-radical polymerization in aqueous solution.

12 Claims, No Drawings

PREPARATION OF WATER-SOLUBLE COPOLYMERS OF AT LEAST ONE WATER-SOLUBLE N-VINYLLACTAM AND AT LEAST ONE HYDROPHOBIC COMONOMER

The present invention relates to a process for preparing water-soluble copolymers of at least one water-soluble N-vinyllactam and at least one hydrophobic comonomer by free-radical polymerization of the monomers in an aqueous solvent, and also to the copolymers obtainable by the process and to their use.

The preparation of copolymers of N-vinyllactams and hydrophobic comonomers by free-radical polymerization is known. For many applications there is a desire for copolymers which form clear solutions in water; in other words, the FNU value of a 5% by weight solution should be $\leq 20$. Such copolymers are prepared in an organic solvent, for example an alcohol, or in a mixture of water and organic solvent having a high solvent content. For instance, U.S. Pat. No. 5,395,904 describes the polymerization of vinylpyrrolidone and vinyl acetate by the feed stream method. An alcoholic solvent is used which may contain up to 50% by weight of water. The polymers are soluble in water, but have a low molecular weight, in the range from 6000 to 50,000 g/mol, corresponding to a K value (in accordance with H. Fikentscher, Cellulose-Chemie, vol. 13, 1932, pp. 58–64) of from 10 to 40.

Copolymerization in aqueous phase, however, would have distinct advantages over the conventional procedures. In the case of free-radical copolymerization, water—unlike alcohols—does not intervene as a regulator, so that copolymers with high molecular weights (K values >50) would be obtainable. It would then be possible to tailor the molecular weight by using appropriate regulators. In addition, deliberately avoiding organic solvents would reduce the costs associated with the production techniques used to date and would enhance their environmental compatibility. Copolymerizations carried out in water have, however, to date not produced the desired copolymers which can be dissolved in water to give clear solutions.

For instance, U.S. Pat. No. 4,520,179 and U.S. Pat. No. 4,554,311 describe the polymerization of vinylpyrrolidone and vinyl acetate, using t-butyl peroxypivalate as initiator, in water or water/alcohol mixtures. The initiator they use permits the preparation of copolymers with a narrow molecular weight distribution but does not lead to water-soluble products with an FNU value $\leq 20$.

DE-A 22 18 935 describes the copolymerization of N-vinylpyrrolidone with various water-soluble and water-insoluble comonomers. The initiators it uses are insoluble in water, and are employed in the form of a fine suspension in an aqueous solution of the copolymers. In the case of the water-insoluble copolymers, this again does not lead to the desired water-soluble copolymers having an FNU value $\leq 20$.

It is an object of the present invention, therefore, to provide a process for preparing copolymers, which can be dissolved in water to give clear solutions, of at least one hydrophilic N-vinyllactam and at least one hydrophobic comonomer by free-radical copolymerization in an aqueous solvent.

We have found that this object is achieved by free-radical polymerization of at least one water-soluble N-vinyllactam of the formula I,

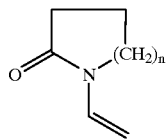

in which
n is 1 or 2 and at least one hydrophobic comonomer having a water-solubility of from 1 to 100 g/l at 20° C. in an aqueous solvent in the presence of an initiator, wherein the initiator used is selected from the group consisting of azo initiators, $H_2O_2$, hydroperoxides in combination with reducing agents, and per-salts, and is added to the reaction mixture in the form of a solution in water and/or in a $C_1$–$C_4$ alcohol.

The novel process is suitable for preparing water-soluble polymers from monomer mixtures whose content of hydrophobic monomers is 10 to 60% by weight, preferably 10 to 40% by weight, based on the monomer mixture. Examples of suitable hydrophobic monomers with a water-solubility of from 1 to 100 g/l are vinyl acetate, vinyl propionate, N-vinylcaprolactam, methyl acrylate, ethyl acrylate, n-propyl acrylate, n-butyl acrylate, t-butyl acrylate, methyl methacrylate, ethyl methacrylate, acrylonitrile and methacrylonitrile.

Suitable initiators for the free-radical polymerization are azo compounds which are appropriate for free-radical polymerization in aqueous solution. Aliphatic and cycloaliphatic azo compounds are particularly suitable, for example 2,2'-azobis(isobutyronitrile),
  2,2'-azobis(2-methylbutyronitrile),
  2,2'-azobis(2,4-dimethylvaleronitrile),
  1,1'-azobis(1-cyclohexanecarbonitrile),
  2-(carbamoylazo)isobutyronitrile, 4,4'-azobis(4-cyanovaleric acid) and the alkali metal and ammonium salts thereof, for example the sodium salt, dimethyl, 2,2'-azobisisobutyrate,
  2,2'-azobis[2-(2-imidazolin-2-yl)propane],
  2,2'-azobis(2-amidinopropane) and the acid addition salts of the two latter compounds, for example the dihydrochlorides.

The water-soluble initiators are particularly preferred.

Other suitable initiators are hydrogen peroxide, hydroperoxides in combination with reducing agents, and per-salts. Examples of suitable hydroperoxides are t-butyl and t-amyl hydroperoxide, cumene hydroperoxide and pinane hydroperoxide, each in combination with, for example, a salt of hydromethanesulfinic acid, an iron(II) salt or ascorbic acid. Particularly suitable per-salts are alkali metal peroxydisulfates.

The amount of initiator used, based on the monomers is from 0.02 to 15 mol-%, preferably from 0.05 to 3 mol-%. In the novel process the initiator is used as a solution, depending on its solubility, in water and/or in a $C_1$–$C_4$ alcohol. The concentration of initiator in these solutions is from 0.02 to 2 mol-%, preferably from 0.1 to 2 mol-%, based on the solvent.

The polymerization medium is water which may contain up to 10% by weight, preferably up to 5% by weight, based on the overall batch, of a $C_1$–$C_4$ alcohol. The quantity of alcohol present in the polymerization medium is preferably only that required for the dissolution and metered addition of the polymerization initiators, some of which only have limited solubility in water. With particular preference, water is used as sole solvent. The polymerization is normally carried out at a neutral pH of 5 to 9. Where necessary, the pH is established and maintained by adding a base, such as ammonia or NaOH, or an acid, such as HCl.

In the novel process the monomers can be introduced into the vessel as initial charge in an aqueous solvent (batch technique). Preferably, however, the monomers, possible as a solution in water and/or a $C_1$–$C_4$ alcohol, are metered in to the reaction mixture (feed stream technique). In the latter case the monomers are metered in such that there is no separation within the reaction mixture; in other words, such that a clear solution is continually present. This makes certain that the hydrophobic monomer is able to react uniformly with the water-soluble N-vinyllactam I. In a particularly preferred embodiment up to 30% by weight, preferably up to 25% by weight, of the water-soluble N-vinyllactam I (based on the total amount thereof) and a small amount of the initiator solution and solvent, preferably water, are introduced as initial charge. The mixture is then brought to reaction temperature and the remainder of the monomers is metered in simultaneously with the rest of the initiator solution and, if desired, with a regulator, metered addition being continuous or taking place in the form of a number of portions. This metered addition is generally carried out over a period of 4 to 14 hours, preferably 5 to 12 hours, ideally 6 to 10 hours. Where N-vinylcaprolactam is used as hydrophobic monomer, it is preferred to operate by the batch technique using water as sole solvent. The monomer concentration in the reaction mixture is from 10 to 40% by weight, preferably from 15 to 30% by weight, based on the reaction mixture. In t his case, after the reaction mixture has been brought to the desired reaction temperature, the initiator solution is fed in continuously or in a number of portions over a period of, in particular, from 1 to 4 hours.

The reaction temperature is generally from 60 to 90° C., but may even be up to 130° C. The reaction can be carried out at atmospheric pressure, autogenous pressure or the superatmospheric pressure of an inert gas. One example of a suitable inert gas is nitrogen. In performing the reaction it should be noted that higher temperatures generally lead to polymers having smaller K values, i.e. lower molecular weights.

The polymers obtained by the novel process are generally of relatively high molecular weight. Where lower molecular weights are desired, they can be produced by adding a regulator to the polymerization batch. Examples of suitable regulators are aldehydes, such as formaldehyde, acetaldehyde, propionaldehyde n-butyraldehyde and isobutyraldehyde, formic acid, ammonium formate, hydroxylammonium sulfate and hydroxylammonium phosphate. It is also possible to use regulators which contain organically bonded sulfur, for example di-n-butyl sulfide, di-n-octyl sulfide, diphenyl sulfide, diisopropyl disulfide, di-n-butyl disulfide, di-n-hexyl disulfide, diacetyl disulfide and di-t-butyl trisulfide. The regulators preferably contain sulfur in the form of SH groups. Examples of these regulators are n-butylmercaptan, n-hexylmercaptan and n-dodecylmercaptan. Particular preference is given to water-soluble, sulfur-containing regulators, for example hydrogen sulfite, disulfites and compounds such as ethyl thioglycolate, cysteine, 2-mercaptoethanol, 1,3-mercaptopropanol, 3-mercaptopropane-1,2-diol, 1,4-mercaptobutanol, mercaptoacetic acid, 3-mercaptopropionic acid, mercapto succinic acid, thioglycerol, diethanol sulfide, thiodiglycol, ethylthioethanol, thio urea and dimethyl sulfoxide. Other suitable regulators are allyl compounds, such as allyl alcohol or ally bromide, benzyl compounds, such as benzyl chloride, and alkyl halides, such as chloroform or tetrachloromethane. In a preferred embodiment the regulator is metered in to the reaction mixture in the form, if desired, of a solution in water and/or in a $C_1$–$C_4$ alcohol.

Following the polymerization reaction, it is preferred to add one or more polymerization initiators to the polymer solution and to heat it, for example, to polymerization temperature or above in order to complete the polymerization. Initiators suitable for this are those azo initiators mentioned above but also all other initiators which are customary and suitable for free-radical polymerization in an aqueous solution, examples being peroxides, hydroperoxides, peroxodisulfates, percarbonates, peroxo esters and hydrogen peroxide. By doing this the polymerization reaction can be taken to a conversion of 99.9%. The solutions produced in the polymerization normally contain 10 to 60% by weight, preferably 15 to 40% by weight of polymer. Following polymerization the resulting solutions can also be subjected to a physical after treatment such as steam distillation or nitrogen stripping, the former removing volatile impurities from the solution.

The aqueous copolymer solutions can be converted to solid powders, if desired, by a conventional drying technique. Suitable drying techniques are those suitable for drying from aqueous solutions. Examples of preferred techniques are spray drying, fluidized-bed spray drying, roller drying and belt drying. Freeze drying and freeze concentration can also be employed.

The K value of the resulting polymers (determined at 25° C. in a 1% strength by weight aqueous or ethanolic solution) is generally from 20 to 100, in particular >40 to 100 and, with particular preference, $\geq 60$ to 100. The determination of K is described in H. Fikentscher "Systematic der Cellulosen auf Grund ihrer Viskosität in Lösung", Cellulose-Chemie 13 (1932), 58–64 and 71–74, and in Encyclopedia of Chemical Technology, Vol. 21, 2nd edition, (1970) 427–428.

It has not hitherto been possible to obtain polymers with a K value $\geq 50$ which form clear solutions in water. The invention therefore additionally provides copolymers which form clear solutions in water, as defined above, and have a K value $\geq 50$.

The measure of water-solubility used is the nephelometric turbidity unit FNU or (NTU), which is measured on a 5% strength by weight aqueous solution of the polymer at 25° C. and is established by calibration with formazine as artificial turbidity agent. The precise method is detailed in the examples below. The polymers obtained in accordance with the invention have an FNU value of $\leq 20$, especially $\leq 10$, preferably $\leq 7$ and especially $\leq 5$.

The polymers obtained by the novel process act firstly at thickeners in aqueous medium and secondly are able to form water-soluble films. They are therefore employed in particular in cosmetic and pharmaceutical formulations, for example as additives or carriers in hair lacquer, hairsetting agents or hair spray; in cosmetic skin preparations, as skin-adhesive gels, or as immunochemicals, for example as catheter coatings. Specific pharmaceutical applications of the novel polymers include, in particular, their use as moist or dry binders, matrix delay agents or coating delay agents (for slow-release administration forms), gel formers, instant-release coatings and film-coating auxiliaries. In addition, the polymers prepared in accordance with the invention can be used as auxiliaries for agrochemistry, for example for seed coating or for soil-release fertilizer formulations, or as auxiliaries in the preparation of fishfood granules.

Owing to the high dispersing action of the polymers prepared in accordance with the invention for both organic and inorganic pigments, the novel polymers are suitable as rust inhibitors or rust removers on metallic surfaces, as scale inhibitors or scale removers, as dispersants in dye pigment dispersions, for example in printing inks. In this context reference may be made to the use of the novel polymers for inkjet recording media, ink pastes and ballpoint pastes.

Also of interset from a technical standpoint is the strong tendency of the novel polymers to form complexes with organic compounds (for example lower hydrocarbons, phenols, tannin and various antioxidants), with enzymes and proteins, or with other organic polymers. In addition, the novel polymers form complexes with inorganic compounds, especially with hydrogen peroxide, halides, metals or metal salts. Accordingly, the novel polymers can be used to remove tannin, phenols, proteins or polyvalent cations from aqueous medium, in ion exchangers, for stabilizing hydrogen peroxide, for example in disinfectants, for stabilizing antioxidants, for example in preservatives, as a polymeric coligand for metal complexes in reversible oxygen absorption, or for catalysts. The novel polymers can be used, furthermore, to stabilize metal colloids. In this context reference may also be made to the use of the novel polymers as noble-metal crystallization nuclei for the precipitation of silver and as a stabilizer for silver halide emulsions.

Additionally, the novel polymers are suitable for modifying surface and interfacial properties. They can be employed, for example, for hydrophilicizing surfaces and can accordingly be used as textile auxiliaries, for example as stripping and levelling agents for textiles coloring, as brighteners in textile printing, etc. Owing to the modifying action for surfaces, the novel agents can be used as coatings, for example for polyolefins, for glass and glass fibers. On the basis of their surface-active effect, they are also used as protective colloids, for example in connection with the stabilizing of metal colloids, or in connection with free-radical aqueous emulsion polymerization. In this context reference may also be made to the use of the novel polymers as auxiliaries in the recovery of petroleum from oil-containing water, and as auxiliaries in the extraction and transportation of petroleum and natural gas. Moreover, the novel polymers find application as auxiliaries in the purification of wastewaters, whether as flocculation aids or in the removal of residues of paint and oil from wastewater. The novel polymers can in addition be used as phase transfer catalysts and as solubility improvers.

The novel polymers are additionally used in the coloring of polyolefins, as color transfer inhibitors, as color mixing inhibitors for photographic diffusion transfer materials, as adhesion promoters for dyes, as lithographic auxiliaries, for photoimaging, for the diazotype process, as metal casting auxiliaries and metal hardening auxiliaries, as auxiliaries for metal quenching baths, as auxiliaries in gas analysis, as a constituent in ceramic binders, as papermaking auxiliaries for specialty papers, as binders in colored paper-coating compositions and as a binder constituent in plaster bandages.

The novel polymers are suitable, furthermore, as proton conductors and can be employed in electrically conducting layers, for example in connection with charge transfer cathodes, as solid electrolytes, for example in solid batteries such as lithium batteries. From the novel polymers it is possible to fabricate contact lenses, synthetic fibers, air filters, e.g. cigarette filters, or membranes. The novel polymers are also used in heat-resistant layers, heat-sensitive layers and heat-sensitive resistors.

The examples below are intended to illustrate the invention without limiting it.

EXAMPLES

The turbidity of the aqueous copolymer solution was determined by nephelometric measurement (modified method in accordance with DIN 38404). In this method the light scattered by the test solution is determined photometrically, this light scattering being caused by interaction between the waves of light and the particles or drops in the solution, the number and size of which determine the degree of turbidity. The measurement unit used is the nephelometric turbidity unit FNU (or NTU) which is measured on a 5% strength by weight aqueous solution of the polymer at 25° C. and is set by calibration with formazine as artificial turbidity agent. The higher the FNU value, the more turbid the solution.

Example 1

Copolymer of 70% by weight N-vinylpyrrolidone and 30% by weight methyl acrylate.

A mixture of 50 g of N-vinylpyrrolidone, 5 g of initiator feed 1 and 1000 g of water was introduced as initial charge into a reactor fitted with stirrer, reflux condenser, gas inlet and two separate feed vessels. This initial charge was flushed with nitrogen and heated to an internal temperature of 70° C. Subsequently, while maintaining the temperature, the monomer feed stream and the initiator feed stream 1 were added simultaneously and at constant rate over a period of 6 hours. The internal temperature was then raised to 75° C. and the initiator feed stream 2 was added, still while maintaining the temperature, over a period of 6 hours. 75° C. was maintained for 2 hours more, and then the reaction mixture was subjected to steam distillation, with about 100 g of distillate being collected. The properties of the clear, viscous polymer solution obtained are summarized in Table 1.

Monomer feed stream consisting of 160 g of N-vinylpyrrolidone and 90 g of methyl acrylate.

Initiator feed stream 1,

Solution of 1 g of 2,2'-azobis(2-amidinopropane) dihydrochloride in 100 g of water.

Initiator feed stream 2,

Solution of 2 g of t-butylperoxypivalate in 40 g of isopropanol.

The pH of the initial charge and of the initiator feed stream 1 was adjusted to 5 using dilute ammonia solution.

Example 2

Copolymer of 60% by weight N-vinylpyrrolidone and 40% by weight methyl acrylate

The procedure of Example 1 was repeated. The properties of the clear, viscous polymer solution obtained are summarized in Table 1.

Monomer feed stream consisting of 130 g of N-vinylpyrrolidone and 120 g of methyl acrylate.

Example 3
Copolymer of 70% by weight N-vinylpyrrolidone and 30% by weight of ethyl acrylate The procedure in Example 1 was repeated. The properties of the clear, viscous polymer solution obtained is summarized in Table 1.

Monomer feed stream consisting of
160 g of N-vinylpyrrolidone and
90 g of ethyl acrylate.

Example 4
80:20 copolymer of N-vinylpyrrolidone and methyl methacrylate

First of all, the following solutions were prepared:
1. Initial charge, consisting of 1000 g of water, 50 g of N-vinylpyrrolidone and 5 g of initiator feed stream 1
2. Monomer feed stream, consisting of 190 g of N-vinylpyrrolidone and 60 g of methyl methacrylate.
3. Initiator feed stream 1, consisting of 1 g of 2,2'-azobis(2-amidinopropane) dihydrochloride, dissolved in 100 g of water.
4. Initiator feed stream 2, consisting of 1 g of 2,2'-azobis(2-amidinopropane) dihydrochloride, dissolved in 100 g of water.

The procedure, the duration and temperature of polymerization and the pH established are as in Example 1. The polymer became insoluble (precipitation and clumping) as early as toward the end of polymerization, but especially during the steam distillation; however, on cooling, a clear and viscous aqueous solution of the polymer developed.

The colorless viscous polymer solution obtained had a solids content of 19.4% by weight, and the K value of the product (as a 1% strength addition in water) was 79.1. Impurities found were <0.005% N-vinylpyrrolidone and 0.1% pyrrolidone. The FNU value of the 5% strength by weight solution in water was 1.5.

Example 5
Copolymer of 70% by weight N-vinylpyrrolidone and 30% by weight vinyl acetate A mixture of
100 g of N-vinylpyrrolidone,
0.2 g of 2,2'-azobis(2-amidinopropane) dihydrochloride,
2 g of aqueous ammonia (25%) and
1000 g of water was placed as initial charge in a reactor fitted with stirrer, reflux condenser, gas inlet and two separate feed vessels. The initial charge was flushed with nitrogen and heated to an internal temperature of 70° C. Then, while maintaining the temperature, monomer feed stream 1 was added at constant rate over the course of 5 hours and, simultaneously, initiator feed stream 1 was added at constant rate over the course of 8 hours. When the addition of monomer feed stream 1 was over, the addition of monomer feed stream 2 was started immediately and was continued at constant rate over a period of 2.5 hours. The batch was then post-polymerized at an internal temperature of 70° C. for one hour more, before the temperature was raised to 75° C. and the initiator feed stream 2 was added at constant rate over a period of 6 hours while maintaining the internal temperature. Following the end of this addition, the temperature was maintained with stirring for 2 hours more. The reaction mixture was then subjected to steam distillation, with 100 g of distillate being collected.

The properties of the clear, viscous polymer solution are summarized in Table 1.

Monomer feed stream 1, consisting of
450 g of N-vinylpyrrolidone
300 g of vinyl acetate
5 g of aqueous ammonia Monomer feed stream 2, consisting of
150 g of N-vinylpyrrolidone
250 g of water Initiator feed stream 1:
Solution of 2 g of 2,2'-azobis(2-amidinopropane) dihydrochloride in 100 g of water Initiator feed stream 2,
Solution of 2 g of 2,2'-azobis(2-amidinopropane) dihydrochloride in 150 g of water.

Example 6
70:30 copolymer of N-vinylpyrrolidone and vinyl acetate (regulated procedure)

First of all, the following solutions were prepared:
1. Initial charge, consisting of 1500 g of water, 100 g of N-vinylpyrrolidone, 0.2 g of 2,2'-azobis(2-amidinopropane) dihydrochloride and 2 g of aqueous ammonia (25%).
2. Monomer feed stream 1, consisting of 450 g of N-vinylpyrrolidone, 300 g of vinyl acetate, 3 g of mercaptoethanol and 5 g of aqueous ammonia (25%).
3. Initiator feed stream 1, consisting of 5 g of 2,2'-azobis(2-amidinopropane) dihydrochloride, dissolved in 150 g of water.
4. Monomer feed stream 2, consisting of 150 g of N-vinylpyrrolidone, 1.9 g of mercaptoethanol and 250 g of water.
5. Initiator feed stream 2, consisting of 2 g of 2,2'-azobis(2-amidinopropane) dihydrochloride, dissolved in 100 g of water.

The procedure, the duration and temperature of polymerization and the steam distillation are as in Example 5.

The colorless viscous polymer solution obtained had a solids content of 28.5% by weight, and the K value of the product (as a 1% strength solution in ethanol) was 37.7. Impurities found were 0.005% N-vinylpyrrolidone and 0.12% pyrrolidone. The FNU value of the 5% strength by weight solution in water was 4.0.

Example 7
Copolymer of 70% by weight N-vinylpyrrolidone and 30% by weight of N-vinylcaprolactam First of all, the following solutions were prepared:
1. Initial charge consisting of 1000 g of water, 210 g of N-vinylpyrrolidone and 90 g of N-vinylcaprolactam.
2. Initiator feed stream: solution of 1.5 g of 2,2'-azobis(2-methyl-butyronitrile) in 30 g of isopropanol.

The initial charge was placed in a stirred laboratory vessel, flushed with nitrogen and heated to an internal temperature of 70° C. Then half of the initiator feed stream was added and the mixture was stirred at an internal temperature of 70° C. for one hour. Then the other half of the initiator feed stream was added, and stirring was continued at the same internal temperature for one more hour. The polymerization temperature was then raised to 85° C., and was maintained at this internal temperature for 3 hours more in order to reduce the amount of residual monomer. The pale yellowish, viscous polymer solution obtained had a solids content of 22.7% by weight, and the K value of the product (as a 1% strength solution in water) was 88.0. Impurities found were 0.011% of N-vinylpyrrolidone and 0.007% of N-vinylcaprolactam. The FNU value of the 5% strength by weight solution in water was 4.3.

Example 8

Copolymer of 50% by weight vinylpyrrolidone and 50% by weight N-vinylcaprolactam First of all, the following solutions were prepared:

1. Initial charge, consisting of 1000 g of water, 150 g of N-vinylpyrrolidone and 150 g of N-vinylcaprolactam.
2. Initiator feed stream: solution of 1.5 g of 2,2'-azobis (2-methyl-butyronitrile) in 30 g of isopropanol.

The procedure and the duration and temperature of polymerization were as in Example 7. The polymer became insoluble during polymerization (precipitation polymerization with precipitation and clumping), but, on cooling, a clear and viscous aqueous polymer solution developed.

The pale yellowish, viscous polymer solution obtained had a solids content of 22.3% by weight, and the K value of the product (as a 1% strength solution in water) was 89.0. Impurities found were 0.014% of N-vinylpyrrolidone and 0.03% of N-vinylcaprolactam. The FNU value of the 5% strength by weight solution in water was 4.3.

Example 9

Copolymer of 50% by weight N-vinylpyrrolidone and 50% by weight N-vinylcaprolactam, regulated procedure 1000 g of water were introduced as initial charge into a reactor fitted with stirrer, reflux condenser, gas inlet and three separate feed vessels, flushed with nitrogen and heated to an internal temperature of 80° C. Then the monomer feed stream, the initiator feed stream 1 and the regulator feed stream 1 were added simultaneously and at constant rate over the course of 3 hours. The reaction temperature was then raised to 80° C., and initiator feed stream 2 and regulator feed stream 2 were added to the reaction mixture at constant rate over the course of 2 hours while maintaining this temperature. The temperature was raised to 85° C. and maintained for 3 hours more. The properties of the resulting, low-viscosity polymer solution are summarized in Table 2.

Monomer feed stream, consisting of 150 g of N-vinylpyrrolidone and 150 g of N-vinylcaprolactam.

Initiator feed stream 1,

Solution of 3 g of 2,2'-azobis(2-amidinopropane) dihydrochloride in 60 g of water.

Initiator feed stream 2,

Solution of 1.8 g of 2,2'-azobis(2-amidinopropane) dihydrochloride in 60 g of water.

Regulator feed stream 1, consisting of 3 g of mercaptoethanol and 30 g of water.

Regulator feed stream 2, consisting of 1.2 g of mercaptoethanol and 30 g of water.

The regulator feed streams were adjusted to pH 6 with dilute sodium hydroxide solution.

TABLE 1

|  | Example 1 | Example 2 | Example 3 | Example 4 |
|---|---|---|---|---|
| Solids content | 19.7% by wt. | 19.9% by wt. | 18.7% by wt. | 35.7% by wt. |
| K value | 73.4 | 69.5 | 71.5 | 62.0* |
| FNU | 3.4 | 5.2 | 6.7 | 3.5 |
| Color Impurities | colorless | colorless | colorless | colorless |
| N-vinyl-pyrrolidone | 0.005% by wt. | 0.006% by wt. | 0.01% by wt. | 0.007% by wt. |
| Pyrrolidone | 0.087% by wt. | 0.117% by wt. | 0.03% by wt. | 0.11% by wt. |

*1% strength in ethanol

TABLE 2

|  | Example 5 | Example 6 | Example 7 |
|---|---|---|---|
| Solids content | 22.7% by wt. | 22.3% by wt. | 29.3% by wt. |
| K value | 88.0 | 89.0 | 23.0 |
| FNU | 4.3 | 4.3 | 3.5 |
| Color Impurities | pale yellow | pale yellow | yellowish |
| N-vinyl-pyrrolidone | 0.011% by wt. | 0.014% by wt. | 0.015% by wt. |
| N-vinylcaprolactam | 0.007% by wt. | 0.03% by wt. | <0.005% by wt. |

Comparison Example 1

Example 1 of DE-A-22 18 935 was repeated, giving a nonhomogeneous, partially coagulated, viscous polymer solution.

Comparison Example 2

Example 3 of DE-A-22 18 935 was repeated, giving an incompletely polymerized and highly turbid polymer solution of low viscosity (FNU>200).

We claim:

1. A process for preparing copolymers in a reaction vessel, which can be dissolved in water to give clear solutions, of at least one water-soluble N-vinyllactam of the formula I,

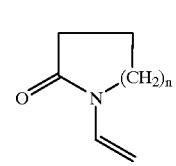

(I)

in which n is 1 or 2, and at least one hydrophobic comonomer having a water-solubility of from 1 to 100 g/l at 20° C. by free radical polymerization in water which may contain up to 5% by weight of $C_1$–$C_4$-alcohol in the presence of an initiator, wherein the initiator used is selected from the group consisting of azo initiators, $H_2O_2$, hydroperoxides in combination with reducing agents and per-salts, and is added to the reaction vessel in the form of a solution in water and/or in a $C_1$–$C_4$-alcohol and wherein from 14 to 30% by weight of the N-vinyllactam is introduced to the reaction vessel as an initial charge and the remainder of the monomers, undiluted or diluted with water and/or a $C_1$–$C_4$-alcohol is metered in to the reaction vessel.

2. The process of claim 1, wherein 10 to 60% by weight based on the overall weight of the monomers, of the hydrophobic monomer is used.

3. The process of claim 1, wherein the hydrophobic comonomer used is vinyl acetate, vinylpropionate, N-vinylcaprolactam, methyl acrylate, ethyl acrylate, n-propyl acrylate, n-butyl acrylate, t-butyl acrylate, methyl methacrylate, ethyl methacrylate, acrylonitrile, methacrylonitrile or a mixture thereof.

4. The process of claim 1, wherein the initiator used is an aliphatic or cycloaliphatic azo compound.

5. The process of claim 4, wherein the initiator used is 2,2'-azobis[2-(2-imidazolin-2-yl)propane], 2,2'-azobis(2-amidinopropane), 4,4'-azobis(4-cyanovaleric acid) or a salt thereof, 2,2'-azobis(isobutyramide), 2,2'-azobis(isobutyronitrile), 2,2'-azobis(2-methylbutyronitrile), dimethyl 2,2'-azobisisobutyrate, 2,2'-azobis(4-methoxy-2,4-dimethylvaleronitrile), 2,2'-azobis(2,4-dimethylvaleronitrile) and/or 1,1'-azobis(1-cyclohexanecarbonitrile).

6. The process of claim 1, wherein the polymerization is carried out in the absence of a regulator.

7. A copolymer with a K value of $\geq 50$, which can be dissolved in water to give a clear solution, which is composed of 40 to 90% by weight of at least one water-soluble N-vinyllactam of the formula I

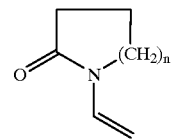
(I)

in which n is 1 or 2, and 10 to 60% by weight of at least one hydrophobic comonomer selected from the group consisting of N-vinylcaprolactam, methyl acrylate, ethyl acrylate, n-propyl acrylate, n-butyl acrylate, t-butyl acrylate, methyl methacrylate, ethyl methacrylate, acrylonitrile, methacrylonitrile, or a mixture thereof having a water-solubility of from 1 to 100 g/l at 20° C.

8. The copolymer of claim 7, having an FNU value $\leq 20$.

9. A cosmetic or pharmaceutical preparation containing at least one copolymer as defined in claim 7 as an auxiliary.

10. An agrochemical composition preparation containing at least one copolymer as defined in claim 7 as an auxiliary.

11. The process of claim 1 wherein part or all of the initiator is metered into the reaction vessel after the initial charge.

12. The process of claim 1, wherein 10 to 40% by weight, based on the overall weight of the monomers, of the hydrophobic monomer is used.

* * * * *